United States Patent [19]

Ohishi et al.

[11] 4,367,345
[45] Jan. 4, 1983

[54] PROCESS FOR PRODUCING TOLYLTHIOUREA HAVING HIGH PURITY

[75] Inventors: Yutaka Ohishi, Shizuoka; Yoshiki Nakayama, Shimizu; Chihiro Yazawa, Yokohama, all of Japan

[73] Assignee: Ihara Chemical Industry Co., Ltd., Tokyo, Japan

[21] Appl. No.: 256,828

[22] Filed: Apr. 23, 1981

[30] Foreign Application Priority Data

May 6, 1980 [JP] Japan ................................. 55-59809

[51] Int. Cl.³ .......................................... C07C 157/09
[52] U.S. Cl. ....................................... 564/26; 564/25
[58] Field of Search ................................. 564/25, 26

[56] References Cited

U.S. PATENT DOCUMENTS

| 2,086,822 | 7/1937 | Schubert et al. | 564/26 |
| 2,254,136 | 8/1941 | Buck et al. | 564/26 |
| 3,282,997 | 11/1966 | Levy | 564/26 |
| 4,049,717 | 9/1977 | Asato | 564/25 X |

FOREIGN PATENT DOCUMENTS 414452  8/1934  United Kingdom .................. 564/25

OTHER PUBLICATIONS

Weller et al., JACS 74, p. 1104 (1952).

*Primary Examiner*—Thomas A. Waltz
*Attorney, Agent, or Firm*—Oblon, Fisher, Spivak, McClelland & Maier

[57] ABSTRACT

A process for producing tolylthiourea having high purity comprises reacting toluidine with a thiocyanate and a mineral acid in the presence of an organic solvent and water.

9 Claims, No Drawings

PROCESS FOR PRODUCING TOLYLTHIOUREA HAVING HIGH PURITY

BACKGROUND OF THE INVENTION

The present invention relates to a process for producing a tolylthiourea. Tolylthiourea are useful as intermediates for dyes and agricultural chemicals. Various processes for production of the same compounds have been proposed. Thus, it has been difficult to produce the same compounds having high purity in a simple industrial process with low cost. The following process have been proposed.

(1) A process using chlorobenzene as a solvent as disclosed in Org. Synth. Coll., Vol. 3, p. 76.
(2) A process using an alcohol as a solvent as disclosed in Japanese Examined Patent Publication No. 17255/1974.
(3) A process using an aqueous solvent as disclosed in Japanese Unexamined Patent Publication No. 148749/1979.

According to the experiments of these processes by the inventors, a production of a by-product of ditolylthiourea has been too much in these processes. The by-product is not easily separated from the product of tolylthiourea to contaminate the product and to give the product having relatively low purity. Even though a crude yield is more than 90% as the process (3), the yeild of the purified product is only up to 80%. In these processes, the yield is also disadvantageously low.

SUMMARY OF THE INVENTION

It is an object of the present invention to provide a process for producing tolylthiourea having high purity under the condition reducing a production of a by-product of ditolylthiourea and easily separating the by-product.

The foregoing and other objects of the present invention have been attained by providing a process for producing tolylthiourea having high purity which comprises reacting toluidine, with a thiocyanate and a mineral acid in the presence of an aprotic organic solvent and water.

DETAILED DESCRIPTION OF THE PREFERRED EMBODIMENTS

The inventors have studied to attain a process for producing tolylthiourea having high purity in high yield wherein the production of the by-product of ditolylthiourea is reduced and the by-product is easily separated. As a result, the present invention has been completed by finding the fact that the object has been attained by the reaction in the presence of an organic solvent and water. That is the present invention is to provide a process for producing a tolylthiourea having high purity by reacting toluidine, a thiocyanate and a mineral acid in the presence of an organic acid and water.

Toluidines used in the process of the present invention can be o-toluidine, m-toluidine and p-toluidine.

Thiocyanates used in the process of the present invention can be alkali metal, alkaline earth metal or organic base thiocyanates, and are preferably, ammonium thiocyanate, sodium thiocyanate, potassium thiocyanate and calcium thiocyanate.

The mineral acids used in the process of the present invention are usually hydrochloric acid and sulfuric acid.

The organic solvents used in the process of the present invention include aromatic or aliphatic aprotic organic solvents such as toluene, dichlorobenzene, o-chlorotoluene, m-chlorotoluene, p-chlorotoluene, xylene, ethylbenzene, cumene, ligroine, hexane, octane, perchlene and chlorobenzene, etc.

In the process of the present invention, the amounts of toluidine, the thiocyanate and the mineral acid can be stoichometric and the amounts of the thiocyanate and the mineral acid can be excess to toluidine. The amount of the organic solvent is not critical and can be 1 to 20 times based on toluidine. The amount of water is preferably more than 0.024 time based on toluidine. Water used in the process can be directly charged with the organic solvent or can be also incorporated in the reaction system by using a part or whole of water for diluting the mineral acid. When concentrated hydrochloric acid is used, water in hydrochloric acid can be used without any addition of the other water. The concentration of the mineral acid is not critical. When water is used for the dilution of the mineral acid, the concentration can be in a range of 10 to 95% preferably 20 to 90%.

The reaction temperature is usually in a range of 20° to 120° C. preferably 60° to 90° C. The reaction time is enough to eliminate toluidine by the reaction, and is usually 1 to 30 hours.

In accordance with the process of the present invention, the reaction of toluidine, the thiocyanate and the mineral acid in the presence of the organic solvent and water whereby the reaction is smoothly performed to reduce the by-production of ditolylthiourea and the by-product of ditolylthiourea is moved into the liquid phase to prevent the contamination of the product. The resulting tolylthiourea can be separated by a simple separating operation such as a filtration. As described above, the product is not contaminated with the by-product of ditolylthiourea to be high purity and the product can be produced in high yield. Therefore, the present invention is effective to produce tolylthiourea having high purity useful as intermediates of dyes and agricultural chemicals in a simple industrial operation with low cost.

The present invention will be illustrated by certain examples and references which are provided for purposes of illustration only and are not intended to be limiting the invention.

EXAMPLE 1

In a reactor, 107.2 g of o-toluidine and 250 ml of o-chlorotoluene were charged and 106 g of 36% hydrochloric acid was charged with stirring. The mixture was heated to 75° C. and 87.5 g of ammonium thiocyanate was admixed with the mixture and the reaction was performed at 75° to 85° C. for 20 hours. The resulting crystal was separated by a filtration and washed with water and dried to obtain 163.5 g of o-tolylthiourea having a melting point of 154° C. The product was analyzed by high speed liquid chromatography to find a purity of 98.0% and an yield of 96.4% as a pure product.

In accordance with the same process except using m-toluidine, m-tolylthiourea having a melting point of 110° C. was obtained.

In accordance with the same process except using p-toluidine, p-tolylthiourea having a melting point of 188° C. was obtained.

REFERENCE 1

In a reactor, 107.2 g of o-toluidine and 250 ml of methanol were charged and 54 g of conc. sulfuric acid was charged with stirring and 87.5 g of ammonium thiocyanate was admixed with the mixture. The mixture was heated to reflux methanol for 20 hours and the precipitate was separated by a filtration and the filtrate was concentrated and washed with water and dried to obtain 149.6 g of o-tolylthiourea. The product was analyzed by a high speed liquid chromatography to find a purity of 74.6% and an yield of 67.1% as a pure product. The purity and the yield were too low.

REFERENCE 2

In accordance with the process of Example 1 except using 107.2 g of o-toluidine, 250 ml of o-chlorotoluene, 51.6 g of conc. sulfuric acid and 87.5 g of ammonium thiocyanate and reacting them at 90° to 100° C. for 10 hours to obtain o-tolylthiourea having a purity of 95.8% (4.0% of N,N-di-o-tolylthiourea) in an yield of 70.6% as a pure product. The separation of ditolylthiourea was not satisfactory and the yield was low.

REFERENCE 3

A mixture of 107.2 g of o-toluidine, 111.4 g of 36% hydrochloric acid and 95.2 g of ammonium thiocyanate was heated at 60° C. for 4 hours and then 70° C. for 4 hours and then 80° C. for 8 hours in ageing and o-tolylthiourea was separated by the same manner. As a result, a product having a purity of 89.4% was obtained in an yield of 84.5% as a pure product. The purity and the yield were too low.

EXAMPLES 2 to 10

In accordance with the process of Example 1, except varying toluidine, the thiocyanate, the mineral acid and the solvents as described in Table, the reactions were performed. The results are shown in Table.

TABLE

| Example | 2 | 3 | 4 | 5 | 6 | 7 | 8 | 9 | 10 |
|---|---|---|---|---|---|---|---|---|---|
| Toluidine | o-TOD | o-TOD | o-TOD | m-TOD | m-TOD | m-TOD | p-TOD | p-TOD | p-TOD |
| Thiocyanate | $NH_4$—TCN | Na—TCN | $NH_4$—TCN | Na—TCN | K—TCN | $NH_4$—TCN | $NH_4$—TCN | Ca—TCN | Ca—TCN |
| mineral acid aqueous solution | HCl aq. | HCl aq. | HCl aq. | $H_2SO_4$ aq. | $H_2SO_4$ aq. | $H_2SO_4$ aq. | HCl aq. | HCl aq. | HCl aq. |
| Solvent | toluene | n-octane | chlorobenzene | o-chlorotoluene | ligroin | dichlorobenzene | perchlene | p-chlorotoluene | xylene |
| Reaction temp. (°C.) | 50–60 | 70–80 | 75–85 | 90–100 | 90–100 | 90–100 | 90–100 | 90–100 | 90–100 |
| Tolythiourea | o-TTU | o-TTU | o-TTU | m-TTU | m-TTU | m-TTU | p-TTU | p-TTU | p-TTU |
| Purity | 99.9 | 98.7 | 99.9 | 99.9 | 99.9 | 99.7 | 98.9 | 99.9 | 99.8 |
| Yield | 95.2 | 98.5 | 97.0 | 96.3 | 98.4 | 96.2 | 95.0 | 95.9 | 95.6 |

Note:
TOD: toluidine
TCN: thiocyanate
TTU: tolylthiourea

We claim:
1. A process for producing tolylthiourea having high purity, which comprises: reacting toluidine with a thiocyanate and a mineral acid in the presence of a combined solvent medium of water and an aromatic or aliphatic aprotic solvent, said solvent medium containing water in an amount of greater than 0.024 times the amount of toluidine.

2. The process of claim 1, wherein the amount of said thiocyanate reacted with said toluidine is at least a stoichiometric amount.

3. The process of claim 1, wherein the amount of said mineral acid which reacts with said toluidine is at least a stoichiometric amount.

4. The process of claim 1, wherein the amount of said organic solvent present ranges from 1 to 20 times the volume of toluidine.

5. The process of claim 1, wherein the reaction is conducted at a temperature of 20° to 120° C.

6. The process of claim 1, wherein said thiocyanate is an alkali metal, alkaline earth metal or organic base thiocyanate.

7. The process of claim 1, wherein said organic solvent is toluene, dichlorobenzene, o-chlorotoluene, m-chlorotoluene, p-chlorotoluene, xylene, ethylbenzene, cumene, ligroine, hexane, octane, perchlene or chlorobenzene.

8. The process of claim 1, wherein said mineral acid is hydrochloric acid or sulfuric acid.

9. The process of claim 5, wherein said reaction temperature ranges from 60° to 90° C.